United States Patent
Ostrow et al.

(10) Patent No.: US 6,564,093 B1
(45) Date of Patent: May 13, 2003

(54) TRANSDERMAL ACTIVE DRUG DELIVERY SYSTEM AND METHOD

(75) Inventors: Alvin Ostrow, Ra'anana (IL); Geert-Henk Koops, Enschede (NL); Joseph Tannenbaum, Jerusalem (IL)

(73) Assignee: Electromagnetic Bracing Systems Inc., Secaucus, NJ (US)

( * ) Notice: Subject to any disclaimer, the term of this patent is extended or adjusted under 35 U.S.C. 154(b) by 0 days.

(21) Appl. No.: 09/807,698
(22) PCT Filed: Oct. 18, 1998
(86) PCT No.: PCT/IL98/00505
§ 371 (c)(1), (2), (4) Date: Aug. 23, 2001
(87) PCT Pub. No.: WO00/23144
PCT Pub. Date: Apr. 27, 2000

(51) Int. Cl.[7] ............................................... A61N 1/30
(52) U.S. Cl. .......................................... 604/20; 604/501
(58) Field of Search ............ 604/20, 501; 607/152–153; 600/362, 573

(56) References Cited

U.S. PATENT DOCUMENTS

| | | | |
|---|---|---|---|
| 4,752,285 A | * | 6/1988 | Petelenz et al. ............... 604/20 |
| 5,080,646 A | * | 1/1992 | Theeuwes et al. ............. 604/20 |
| 5,279,543 A | * | 1/1994 | Glikfeld et al. .............. 600/395 |
| 5,746,711 A | * | 5/1998 | Sibalis et al. ................. 604/20 |

* cited by examiner

Primary Examiner—Mark Bockelman
(74) Attorney, Agent, or Firm—Edward Langer; Shiboleth, Yisraeli, Rober, Zisman & Co.

(57) ABSTRACT

A transdermal drug delivery system having at least one patch (20) with an electrosmotic, electro porous membrane (26) comprised of an inert biochemical substance which becomes actively electro-osmotic when an electric charge is passed through the membrane enabling a drug solution passing through to a skin surface to create an electroporative effect. The patch may be powered by a battery, an external power source (82), or self-powered by an auto-bio-fuel cell which acts as a battery during drug solution saturation. Multiple patches may be configured as a linked patch unit for use with a flexible cuff apparatus (70) to provide circumferential treatment of a body part. A network of supply tubes (66) may be connected to an external reservoir (68) to provide a slow supply of medicated fluid to each patch. A titration regulator (72) is in communication with the transdermal patch to regulate permanent flow to the skin.

38 Claims, 8 Drawing Sheets

TRANSDERMAL ACTIVE DRUG DELIVERY SYSTEM AND METHOD

FIELD OF THE INVENTION

The present invention relates generally to medical appliances and especially to the application of electrically charged porous patches in fluid communication with a drug medium and to a uniform system of an electrophoretic pharmaceutical delivery cuff apparatus for transdermal drug delivery.

BACKGROUND OF THE INVENTION

The use of iontophoresis and electrotherapy for drug delivery has been known and recognized as an acceptable form of treatment. Prior devices utilizing iontophoresis and/or electrophoresis were unable to simultaneously treat large areas systematically in an anatomical circumference or be incorporated under casts or braces, with the exception of U.S. Pat. No. 5,344,384 to one of the co-inventors of the present invention.

Furthermore, the previously known devices did not provide the availability of multiple treatment protocols.

Many iontophoretic drug delivery devices have been described in the patent literature, including U.S. Patent Numbers:
U.S. Pat. No. 5,387,189 to Gory et al;
U.S. Pat. No. 5,358,483 to Sibalis;
U.S. Pat. No. 5,356,632 to Gross et al;
U.S. Pat. No. 5,312,325 to Sibalis;
U.S. Pat. No. 5,279,544 to Gross et al;
U.S. Pat. No. 5,167,479 to Sibalis;
U.S. Pat. No. 5,156,591 to Gross et al,
U.S. Pat. No. 5,135,479 to Siballs et al;
U.S. Pat. No. 5,088,977 to Sibalis;
U.S. Pat. No. 5,057,072 to Phipps;
U.S. Pat. No. 5,053,001 to Reller et al,
U.S. Pat. No. 4,942,883 to Newman;
U.S. Pat. No. 4,752,285 to Patelenz et al;
U.S. Pat. No. 4,734,090 to Sibalis;
U.S. Pat. No. 4,731,049 to Parsi;
U.S. Pat. No. 4,622,031 to Sibalis,
U.S. Pat. No. 4,325,367 to Tapper; and
U.S. Pat. No. 4,164,226 to Tapper.

The need to provide a broad spectrum of treatment protocols suited to the injury and/or medical condition of the patient requires a system having a high degree of drug flow controllability.

Controlled delivery of drugs through the skin by use of transdermal patches is well known in the prior art. Passive transdermal drug delivery systems provide advantages over other drug delivery methods by delivering the drug directly to the affected area. This method is advantageous over other known methods such as oral administration which necessitates absorption through the digestive tract, or intravenous drug administration which involves needles. Currently, certain patient types present serious problems to traditional IV techniques. These patients include: patients with blood disorders, immuno-compromised patients, patients with renal dysfunction, patients with vein disorders or deep set veins and small children. It is estimated that patients in the above categories represent at least 20–25% of all hospital patients. Both oral and intravenous administration involve administering high doses of drugs to the body at one time, systemically affecting the whole body with the pharmaceutical. These high levels of drug concentration in the blood can create toxic side effects. In addition, only a very small percentage of the drug reaches the affected target area in the body.

There has been a trend toward demands for new methods of self-administered prescription pharmaceuticals such as time-release oral medications and transdermal patches. Transdermal delivery provides medication specifically to the area of treatment in the exact quantities required. However, the number of passive transdermal drug delivery systems available, such as the nicotine, estrogen and nitroglycerine patches, are limited because they are effective only with small-molecule drugs. Many of the newly developed proteins and peptide drugs are too large to be delivered through passive transdermal patches, forcing pharmaceutical companies to seek advanced delivery technology such as electrical assist (ionotophoresis) for large-molecule drugs.

Iontophoresis is a technique employed for enhancing the flux of ionized substances through membranes by application of electric current. One example of an iontophoretic membrane is given in U.S. Pat. No. 5,080,646 to Theeuwes. The principal mechanisms by which iontophoresis enhances molecular transport across the skin are (a) repelling a charged ion from an electrode of the same charge, (b) electroosmosis, the convective movement of solvent that occurs through a charged pore in response the preferential passage of counter-ions when an electric field is applied or (c) increase skin permeability due to application of electrical current.

Many drugs have been formulated for commercial use in the pharmaceutical industry employing iontophoresis. Both passive and electrical assist transdermal drug delivery necessitate wearing transdermal patches made of synthetic substances consisting of a high co-polymer content for long periods of time, often causing skin reactions due to the body's rejection of the membrane as being foreign to the skin. Also, most membrane patches require a specific drug designed toward use with a particular membrane for a specified limited time of usage. Iontophoresis often requires cumbersome electrical connections to external power sources, which may be stationary or portable which can confine the patient's activity.

Patients are often required to wear casts or braces over long periods of time. This limits access to the treatment area, making additional medical treatment more difficult while the limb is immobilized. Atrophy of the underlying muscle tissue is a common problem. Because of the inaccessibility of the treatment area, drug delivery is made difficult, and traditional methods of drug delivery by injection must be used.

Therefore, it would be desirable to overcome the above-mentioned disadvantages and provide an unencumbered self-powered transdermal patch system for drug delivery that would deliver large-molecule drugs in an efficient manner directly to the affected site, even under a cast or brace, while allowing long term skin contact without causing skin irritation or allergic reaction.

OBJECTS OF THE INVENTION

Accordingly, it is a principal object of the present invention to overcome the disadvantages of prior art devices and systems and provide a transdermal drug delivery system of the general character described herein which is not subject to the aforementioned deficiencies.

A further object of this invention is to provide a transdermal drug delivery system having selective curative regimens that can be applied severally or together.

Another further object of this invention is to provide a transdermal drug delivery system that can be worn comfortably by the patient, as a lightweight, portable design that is cost effective to manufacture and does not encumber motion by the patient.

Another object of this invention is the capability to deliver any drug in a fluid medium having either a positive or a negative molecular valence through the skin, iontophoretically.

Many drugs have been formulated for use in iontophoretic systems, and others are being experimented with and developed by the pharmaceutical industry for the feasibility of their delivery via iontophoresis for commercial use (e.g., nicotine, antihistamines, beta-blocker, calcium channel blockers, non-steroidal, anti-inflammatory drugs, contraceptives, anti-arrhythmic drugs, antivirals, hormones, alpha-interferon and chemotherapeutic anti-cancer agents). Therefore, it is also an object to incorporate porous membranes having pores that can accommodate molecular drug weights from one to 50,000 Daltons, or greater.

Yet another object of this invention is to optimally produce a selected alternating positive and negative electrical charge from a controlled power source/console switch, thereby creating the electrical field polarity which is responsible for providing the "ionic drive" mechanism needed to modulate either anode or cathode drug delivery within the patch devices. The ionic drive mechanism is the force behind the electrochemical phenomenon of iontophoresis required to propel, infuse and deliver a pharmaceutical medium in accordance with its polar molecular valence through the surface of the skin by means of electroosmosis. The success of administering the fluid medium depends on the negative or positive valence of that medium for anode or cathode delivery.

It is another object that the invention can provide electromagnetophoresis. Scientific information supports the concept that electromagnetic fields (EMFs), in combination with drug delivery, can either increase the osmotic penetration of drugs through the skin known as "magnetophoresis", or that EMFs may help accelerate the effectiveness of exogenous drugs after being introduced into the body by transdermal or hypodermic methods. Exposure to PMF (Pulsed Magnetic Field) immediately after administration of methotrexate or mitomycin C, pharmaceutical anti-tumor agents, into the cell increases eddy current stimulation induced by PMF, and the cell cycle shifts from the non-proliferative to proliferative phase, resulting in increased anti-tumor activity.

It is another object of to provide combined therapy, where the combination of magnetotherapy, electrotherapy and iontophoresis heighten the effectiveness of electrochemotherapuetic treatment to a target area used for electrochemotherapy (ECT). The combination of multiple drivers to produce an electrochemotherapeutic effect is known as "electro-infusion".

It is also another object of the invention to provide a membrane electrode with a biosensing component that can detect flow rate over time and the amount of permeant flow through the skin and the membrane for the control of any number of drug permeants, severally, or in combination.

Another object of the invention is to create a membrane electrode with a layered structure comprising:

1. a microtitration foam layer in contact with a permeant supply superior to an electrode. This foam layer is intended to prevent leakage or seepage, and to ensure slow feed of the permeants traversing the porous membrane layer below; and
2. a porous electroconductive membrane layer or membranes with electroconductors; and
3. a biosensor or biosensors interconnected with the transdermal membrane junction to the skin which are placed as to allow the permeation of pharmaceutical fluids.

It is also an object of this invention to create a variety of configurations for transdermal drug delivery, whereby the patch is constructed of different sizes and shapes.

Another object of this invention is to provide an electrophoretic cuff apparatus that can fit under a cast or brace. A foam fabric can be used on the superior external surface of the apparatus, adding to patient comfort.

It is also an object of this invention to create a variety of configurations for constructing the cuff, whereby the cuff is constructed by the interconnecting of the membrane electrodes or can be constructed merely as a housing matrix for the electrodes.

SUMMARY OF THE INVENTION

Accordingly, it is a principal object of the invention to provide a transdermal patch system for drug delivery which is non-irritating to the skin while administering a broad range of drugs.

In accordance with a preferred embodiment of the invention there is provided a transdermal patch system for delivery of a pharmaceutical medium comprising:

a stored energy source for generating an electrical current;

means for generating an electromagnetic field having at least one predetermined frequency means for activating said energy source to generate said current producing said electromagnetic field;

a layer of permeable foam for retaining therein a quantity of pharmaceutical medium exhibiting at least partial ionization; and an electroconductive membrane disposed under said foam layer through which the pharmaceutical medium passes, said electromagnetic field driving said ionized pharmaceutical medium by active transport through said membrane to provide drug treatment therapy via the skin.

In a preferred embodiment of the present invention the transdermal drug delivery system is provided as an unlinked patch device with an electroosmotic, electroporous membrane comprised of an inert biochemical substance which becomes actively electroosmotic when an electric charge is passed through the membrane. During iontophoresis, an electric current is passed into the membrane, and it becomes electro-bioactive enabling drug solution to be passed through the electrode membrane wall to a target area on the skin surface creating an electroporative effect.

In a preferred embodiment, the patch is self-powered by an autobiofuel cell for providing the electricity for iontophoresis through the membrane. The autobiofuel cell is comprised of a biochemical fuel cell substance creating a battery power source, causing an electric charge to be passed through the inert membrane which is saturated with a drug solution. The autobiofuel cell is activated by pressing on an "activation button" causing a mix of chemical compounds which are released into the main fuel cell to activate the electric conductivity of the power drivers. An indicator is provided for indicating when the battery power source is low.

In another preferred embodiment, a female jack is provided on the top surface of the patch for either giving a temporary charge to the fuel cell when the battery is low or may be used on a more long-term basis for connection to an external power source. A portable 9V battery or stationary wall power pack may be supplied to accomplish the recharging.

The electric current from the autobiofuel cell or the external power source is passed through an intermediate electromagnetic/electroconductive separation plate, transmitting the power drivers for iontophoresis and/or magnetophoresis. The combination of both iontophoresis and magnetophoresis results in electroinfusion (c) by energizing the drug reservoir membrane from the autobiofuel cell or external power source, creating an electroosmotic electrobioactive phenomenon transferring the permeant through the membrane layer to the treatment area. The separation plate prevents seepage and interaction of the autobiofuel cell fuel with the membrane and treatment area.

Control of the drug delivery with a porous membrane is difficult. Control must be accomplished by the membrane and not the skin. A completely porous membrane would have too low a transport resistance causing the skin to be the rate determining factor. Therefore, in a preferred embodiment, a dense coating layer is provided on the porous membrane support. Since most of the drugs that have to be delivered by the transdermal system are charged, the dense coating layer is provided with a mosaic structure such that it contains positive and negative fixed charges to accommodate differently charged drug solutions.

Parameters of the patch can be altered to accommodate specific needs of specific drug solutions. These parameters include: drug concentration, current density, membrane thickness and charge density of the fixed charges in the membrane.

In addition, the membrane is impregnated with a substance on the epidermal delivery layer to cause hyperpermeability of the permeant through the stratum corneum (SC) of the skin and into deeper body tissue layers. The SC is a thin layer of highly resistant tissue with the underlying viable dermis exhibiting a much lower resistance. The membrane is laced with acetylcholine, epinepherine or other stimulants to enhance permeability through the SC.

The dermal contact surface of the membrane is constructed out of substances close to the structure of human skin, based on the membranes used in artificial kidney membranes such as sulfonated polysulfone (PSF), so as to be non-irritating. In addition, the membrane can be constructed using components of bioenegineered artificial skin compounds (such as Apligrafs from Organogenesis, Inc.). This will reduce skin rejection of polymers currently used to accomplish transdermal transport of drug solutions. Alternatively, any commercially available transdermal membrane can be used with the patch (for example, IonClad R1010, R1030, R4010 or R4030 from Pall Corp., Port Washington, N.Y.). The patch can be used to treat open or closed wounds.

An electrophoretic tube port is provided on the external side of the patch for injection of a needle-less syringe to provide the drug solution as needed. Thus one type of disposable patch can be provided and filled with any of a variety of different drugs as needed. The drug solution is then transferred to and stored in a miniature reservoir in the patch. The reservoir can be provided as a foam layer for controlled microtitration. In another preferred embodiment, the patch is provided with a connection to an external, metered titration system. Alternatively, the port can be used to connect a standard IV drip bag via electrophoretic tubing.

In another embodiment of the present invention the patch is provided with a biosensor for sensing when the drug is no longer present and alerting the patient or physician via an audible or visual signal.

In still another preferred embodiment, a microswitch is provided to adjust and create electrical and electromagnetic frequencies of varying and alternating intensities and time cycles of a wide range to match the valences of the variety of drugs. The patch would be supplied with a microprocessor for storing and controlling the various settings. Drugs may be permeated through the transdermal membrane and the skin either singularly or in multiple combination, according to the programmed settings. The current density used is less than 0.5 mA/cm$^2$ of the transdermal membrane electrode surface that is applied to the skin. Connections may also be provided for receiving input from the biosensors and controlling delivery from an external processor.

The transdermal patch of the present invention can be used in conjunction with an electrophoretic cuff apparatus which encompasses the construction of a preform applicator wrap enclosing one or more transdermal patches to pass a liquid drug medium through the skin and surface tissues. The electrical current may be supplied by the autobiofuel cell or through an external source. The applicator wrap is externally self-supported, contiguous to a body surface to form a preform wrap or cuff.

In particular, the electrophoretic cuff apparatus concerns an electrotherapy apparatus incorporated within or without a cast or orthotic brace or preform that delivers ancillary treatment modalities which are provided by an optional Neuromuscular Electrostimulation, Transcutaneous Nerve Stimulation (T.E.N.S.) and Interferential Electrotherapy component. The preform forms a "cuff" that can be wrapped around the body in different sizes and sections for easy treatment of large and small anatomical areas. The cuff is connected to a Velcro attachment to latch on the sections, to deliver the fluid medium and electrical charge.

The construction of the apparatus is important for regulated consistent uniform drug therapy around the circumference of a body part to increase efficiency of drug therapy application. Optionally, biosensors and an external pump regulated titration system can ensure precise regulation of drug flow transdermally through the skin and the transdermal membrane electrodes that act as a conduit reservoir for the flow of medicated permeants being supplied by a continuous source reservoir.

In addition to the application of electric energy in the present invention, a pulsed or continuous electromagnetic field is created by a separate circuit. When a medicament is added to the aqueous environment, the invention becomes a drug delivery apparatus with a variety of protocols for iontophoretic and electromagnetophoretic delivery systems.

When the cuff apparatus is not used for drug delivery, it can be applied and worn while the patient is exercising or conducting the activities of daily living.

The cuff wrap matrix is formed of waterproof, molded and flexible plastic, styrofoam or canvas-like material to accommodate a continuous hook-up for additional preform patches of various sizes and shapes, as required, to encompass the circumference of a desired target treatment area, thereby creating a "cuff" or wrap around any anatomical body part.

The wrap is provided with a network array of electrically conductive porous polymer membrane electrode patch devices providing a "checkerboard" pattern of alternating positive and negative polarities.

The patches can be energized by galvanic and electromagnetic current drivers to propel permeant drugs through means of either iontophoresis, magnetophoresis or combined electromagnetophoresis.

A feature regarding the present invention of the electrophoretic cuff is that it can have multiple uses beyond its use for introducing drugs transdermally. Thus, the present invention provides, in a versatile fashion, a variety of therapeutic benefits and applications with electrical energy modes for nerve stimulation, pain sedation and the prevention of atrophy. Additionally, when configured as a therapeutic garment, the mode of Electrical Muscular Stimulation (EMS) can be introduced during physical therapy exercises, weight training for neurologically impaired and atrophic muscles, etc.

It should be apparent that the multi-modal nature of this apparatus covers a broad spectrum of treatment protocols, including the treating of injuries to soft tissues, as well as arthritis of joints at selected locations of the human and mammalian bodies.

The patches within the cuff provide a consistent supply of medication, to bathe the body part in a continuous fluid within a circumference, whereas other electrical transdermal drug delivery methods are not as easily accessible or applicable. This system also allows for transdermal drug treatment simultaneously to more than one location where medical attention is needed. In addition, a non-medicated fluid can also be used to moisten the porous electrodes as an electrolyte, to assist electrical conductivity when the apparatus is being used for purposes other than drug delivery.

In addition, the patch can apply continuous fluid medium from an optional external reservoir similar to intravenous (I.V.) applicators, but without the use of a hypodermic needle. The patch can be used, with or without the cuff, as an option to replace traditional methods of postoperative analgesia, such as intramuscular injections. The patch has benefits for those patients who dislike hypodermic needle injections or have medical conditions making intravenous drug delivery difficult.

Furthermore, when using the external reservoir, the delivery of drugs transdermally can be regulated and monitored through a computer chip and "pump" administration system that records the titration rate, amount and dosage of medication supplied. The pump can vary the speed of introduction of the transdermal permeant at a desired rate.

The pump administration and titration mechanisms are interactively connected to biosensor detection sensors located within the transdermal membrane patch devices. Signals from the membrane electrode biosensor monitor the drug flow rate of permeant being transported through the skin as well as the membrane electrode. The pump/titration regulator receives these signals from the membrane biosensor to regulate exact controlled increments of the permeant being delivered to the surface of the skin with an even flow pressure distribution in the electrophoretic tubing and membrane electrodes in the cuff delivery system. Alternatively, a roller clamp can be used to clamp I.V. tubing to control the flow of the pharmaceutical permeant.

In view of the above, it should be apparent that the present invention provides many advantages and overcomes many of the shortcomings and disadvantages of the prior art, while providing an improved apparatus.

Additional features and advantages of the invention will become apparent from the following drawings and description.

BRIEF DESCRIPTION OF THE DRAWINGS

For a better understanding of the invention with regard to the embodiments thereof, reference is made to the accompanying drawings, in which like numerals designate corresponding elements or sections throughout, and in which.

DETAILED DESCRIPTION OF THE PREFERRED EMBODIMENTS

With specific reference now to the figures in detail, it is stressed that the particulars shown are by way of example and for the purpose of illustrative discussion on the preferred embodiments of the present invention only, and are presented in the cause of providing what is believed to be the most useful description principles and conceptual aspects of the invention, based upon the medical literature. In this regard, no attempt is made to show structural aspects of the invention in more detail than is necessary for a fundamental understanding of the invention, the description taken with the drawings making it apparent to those skilled in the art how the several forms of the invention may be embodied in practice.

Figure 1:
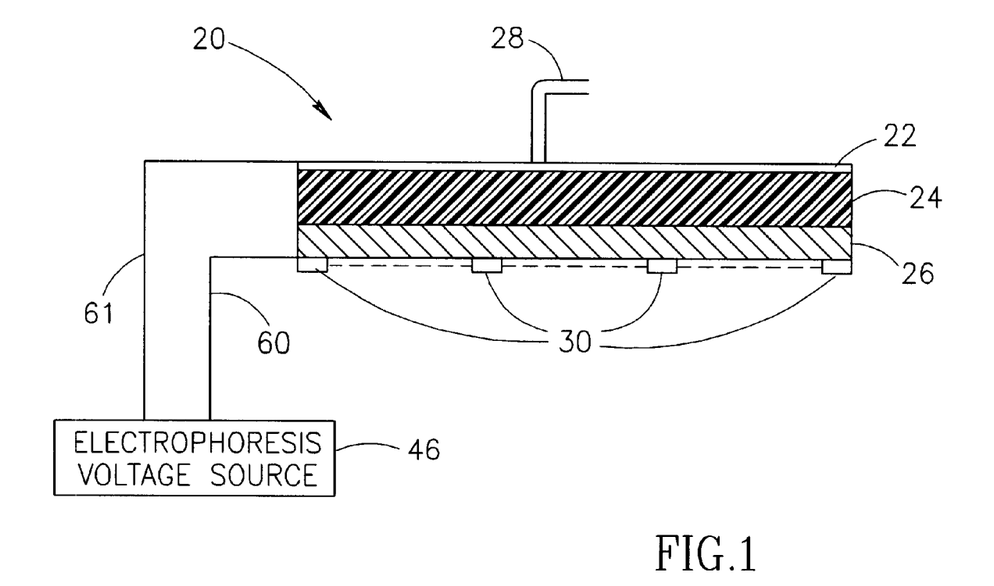
FIG. 1 is a cross-section showing a transdermal patch device of the present invention divided into functional sections.

Referring now to FIG. 1, there is shown a cross-sectional view of transdermal patch device 20. Transdermal patch device 20 comprises at least a three layer structure, including sealant 22, microtitration foam 24 and membrane 26. Sealant 22 is on the superior aspect and connects with electrophoretic tubing port 28. Inferior to sealant 22 is microtitration foam 24. Foam 24 assists in permeant delivery timing and prevents excess permeant from running off. The foam may be cultured, dehydrated and/or gamma irradiated to ensure that biological contamination is prevented. The foam binds to membrane 26.

Membrane 26 is formed of an electrically woven fabric which is treated with antibiotic and antifungal chemicals to prevent biological contamination. The membrane itself is commercially available (for example, IonClad R1010, R1030, R4010 or R4030 from Pall Corp., Port Washington, N.Y.) and made of polymers that have ultra-filtration properties of 100,000 to 200,000 molecular weight cut-off and 2 nm to 1 µm pore size to accomodate drugs of a high molecular weight. Membrane 26 can also be provided as an electroconductive porous polymer or co-polymer. The large molecular weight cut-off allows drugs such as insulin (MW 6000), heparin (MW 6000–30,000), plasma factors (MW over 50,000).and anti-cancer drugs to be used with the system. Multiple drug delivery of large and small size drugs is possible. Membrane 26 acts as a reservoir and is encased in a barrier to prevent uncontrolled leakage of the drug. Membrane 26 is electro-conductive to provide for electro-phoresis and other treatment modalities.

In addition, membrane 26 is provided with a substance on the epidermal delivery layer to cause hyper-permeability of the permeant through the stratum corneum (SC) of the skin and into deeper body tissue layers. The SC is a thin layer of highly resistant tissue with the underlying viable dermis exhibiting a much lower resistance. The membrane is laced with acetylcholine, epinepherine or other stimulants to enhance permeability through the SC.

Biosensors 30 are disposed inferior to membrane 26, on the skin surface, and are connected to the computerized titration system to sense the flow rate of permeant through the SC. Biosensors at the junction of the transdermal membrane and the skin surface are an integral part of the intelligent feedback titration supply system which controls the exact flow of drugs from the reservoir, as they detect, monitor and register drug concentration and absorption into the skin.

Additionally, the biosensor of the present invention can be provided to detect concentration of blood glucose, hormones and endogenous drugs (such as insulin). For example, in diabetics this feature is important for proper dosage and delivery of drugs such as insulin, by biosensing the blood glucose or insulin levels in the blood, so as to determine how much insulin must be administered by the intelligent feedback titration and monitoring system for transdermal delivery of an exact therapeutic dosage.

Figure 2:
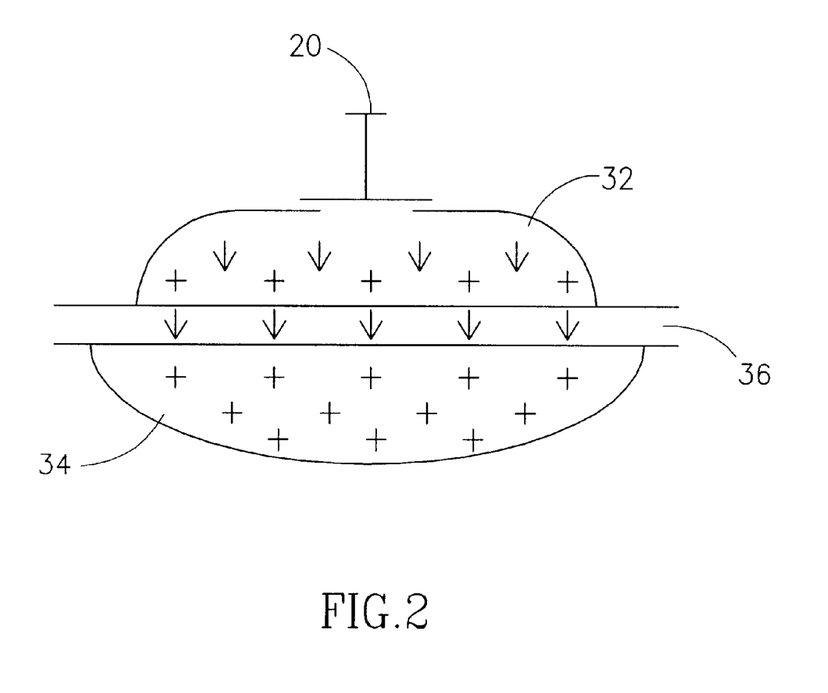
FIG. 2 is a diagram showing the flow of permeant through the skin surface.

FIG. 2 depicts the flow of permeant through the skin surface 32 to an area 34 of increased concentration, in response to transdermal patch device 20. Dry skin has a low resistance (as low as 2.5 microohms/cm$^2$), and SC 36, having a lower water content (20%) than other epidermal cells (about 70%), represents a less conductive medium. Penetration through the SC is the rate determining step in transdermal drug absorption. This biological phenomenon has been the source of variability in the determination of appropriate dosage for ion transfer. The adjustment of the dosage parameters is essential to provide optimal transfer of the ionized medication while insuring the safety of the patient. Transport rate (T) can be affected by the type of membrane used, the skin type, the current density applied and the feed concentration of the drug. Calculation of the transport rate (T) can be accomplished via the formula:

$$T=g/(m^2 \times hr)$$

where g=weight of drug being transported, m$^2$=area to which patch is applied, and hr=time of application.

Biosensor 30 can be constructed to comprise three electrodes which are saturated with normal saline. The first biosensor electrode serves as the reference electrode and is situated far from the treatment area. The second biosensor electrode is localized exactly above the treatment area and is the analyzing electrode. The third biosensor electrode is near the reference electrode for comparison purposes. A sensitive millivolt meter measures the voltage between the reference electrode and the comparison electrode. Then the difference is measured between the reference electrode and the analyzing electrode. The difference in millivolts between the two measurements is the actual concentration gradient. Using the skin resistance value the final value can be extrapolated. The system needs to be calibrated for each drug.

Figure 3:
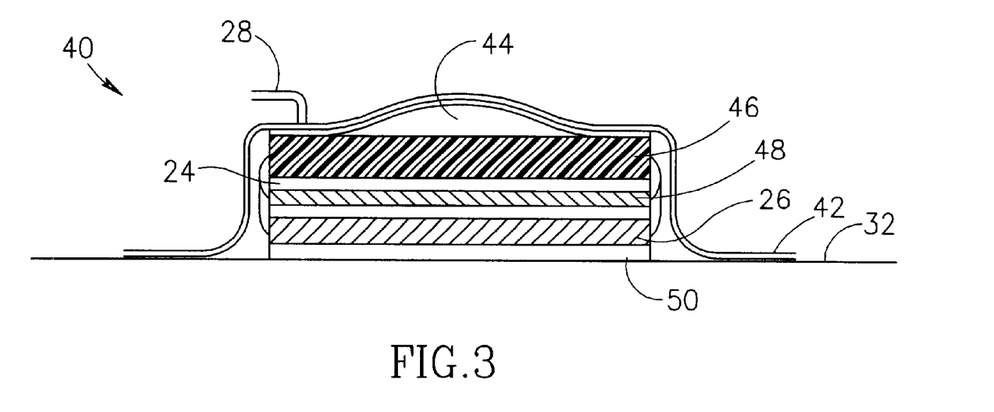
FIG. 3 is a cross section of a self-powered transdermal patch device illustrating its functional sections.

Referring now to FIG. 3, there is shown a cross-section of an autobiofuel powered transdermal patch device 40. At least one of patch 40 is secured to skin surface 32 by adhesive tape 42. Patches 40 can be arranged as needed on adhesive tape 42 to provide circumferential treatment of a limb in a cuff format. Extending through adhesive tape 42 is electrophoretic tubing port 28 for insertion of a drug solution. Microtitration foam 24 acts as a reservoir upon insertion of the drug solution. Foam 24 assists in permeant delivery timing and prevents excess permeant from running off. The foam may be cultured, dehydrated and/or gamma irradiated to ensure that biological contamination is prevented.

Upon depression of activator button 44, a mix of chemical compounds are released into autobiofuel cell 46 to activate the electro-conductivity of separation plate 48. For example, this can be accomplished with a suitable construction for a water activated dry-cell storage battery. Alternatively, this can be accomplished using a rechargable battery where the activator button serves as a mechanical or electrical switch to close the circuit. The power drivers are supplied as separation plate 48, allowing both iontophoresis and magnetophoresis. Separation plate 48 gives a specific frequency of cathodal field designed to push the ionic drug solution through skin surface 32. In magnetophoresis, magnetic fields are employed to influence chemical reactions in ion transport. An impulse electromagnetic field with approximately a 1 ms impulse, 10 Hz frequency and 1–10 mT magnetic induction has been found to be effective. Drugs can be delivered to a specific target area without being dispersed into the system's circulation for as long as the magnetic field is maintained. Use of magnetic carriers has been proven effective, for example, in site specific delivery of chemotherapeutic agents in cancer therapy. Use of magnetic fields increases cell permeability. In addition, magnetophoresis has been shown to enhance metabolysis of drugs such as anti-tumor medications methotrexate and mitomycin C. Use of an electromagnetic field generator would allow drugs which have a large dipolar moment, a permanent charge or a ferro group to be attracted to a central region of the field.

In order to enable an infusion of a multiple amount of drugs for multi-use purposes transdermally, a power generator will generate various modulated electrical and electromagnetic field intensities, alternating polarities, timing and strengths that can be automatically, consecutively, and/or specifically programmed and are employed to correspond to the varying valences and atomic weights of pharmaceuticals for transdermal active transport through the membranes and dermal layers. The range of pulse intensities and magnitudes is built into the pulse generator as the drivers. The drivers are responsible for inducing the bioactivity of the membrane electrodes, the electro-introduction of drugs through the electrode, and the electro-infusion effect of accelerating drug delivery through the SC and deeper tissues.

Separation plate 48 additionally acts as an impermeable conductive barrier preventing membrane 26 and skin surface 32 from coming into contact with leakage of caustic and dangerous ionic electrochemicals while still conducting electricity.

Additionally, membrane 26 may be composed of hypoallergenic materials close to the structure of human skin, developed from the materials used in artificial kidney membrane such as sulfonated polysulfone (PSF) or polyetheretherketone (PEEK), so as to be nonirritating. In addition to the use of an artificial kidney membrane, the membrane can use components of bioengineered artificial skin compounds (e.g. Apligrafs from Organogenesis, Inc.). This will reduce skin rejection of polymers currently used to accomplish transdermal transport of pharmaceuticals.

Figure 4:
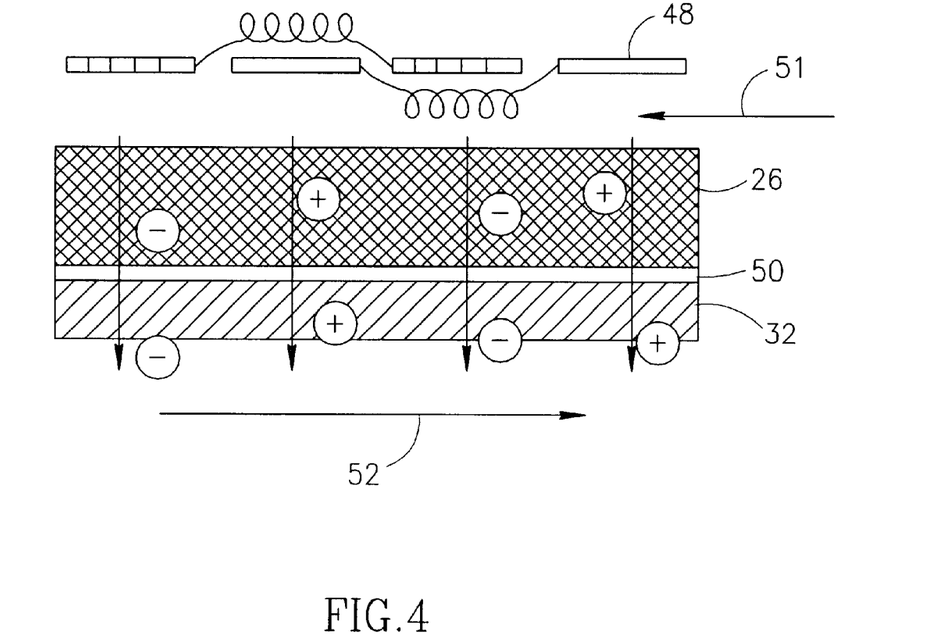
FIG. 4 is a diagram showing a schematic representation of a multi-drug system where the transport resistance is determined by the dense charged mosaic layer.

Controlled delivery of the drug solution is necessary. Dense coating layer 50 on membrane 26 acts as the rate determining factor in delivery of the drugs. Dense coating layer 50 is provided as a mosaic of positive and negative fixed charges to accommodate both anionic and cationic drugs. This is shown in further detail in FIG. 4. Separation plate 48 provides the push for drug solutions of various charges to transverse porous membrane 26 and reach dense coating layer 50 with its mosaic fixed charges. Drug solution 51 passes through dense coating layer 50 in a controlled fashion, to reach skin surface 32. Drug solution 51 passes through skin surface 32 and into bloodstream 52. A feature of the invention (shown in FIG. 1) is that biosensors 30 are disposed inferior to membrane 26, on the skin surface, and can be connected to an indicator on the surface of patch 40 or optionally connected to an external computerized titration system to sense the flow rate of permeant through the SC.

Thus, autobiofuel powered transdermal patch device 40 provides a patch which extends significantly the range of drugs for which transdermal delivery is a viable administration route. The patch can deliver a wide variety of types and sizes of drugs, up to 6000 Dalton or greater, without attachment to an external power source. Drugs can be administered in combination or sequentially, according to a treatment protocol. The patch can be provided as a one-use disposable unit. The use of iontophoresis reduces application time even for drugs currently being used in passive patches, reducing potential irritation. The patch can be supplied with a membrane which reduces irritation by being composed of material used in synthetic human tissues and by being treated to be bacteriostatic. Alternatively, a variety of commercially available membranes can be used as determined by the drug being applied. The patch can be used for local treatment or combined as a multiple set of patches by the use of an adhesive into any configuration, including those providing cumulative drug treatment with an electrophoretic cuff apparatus. The patch can be used for active transdermal drug delivery, and will also function in passive drug delivery where no electrical current is used.

Figure 5:
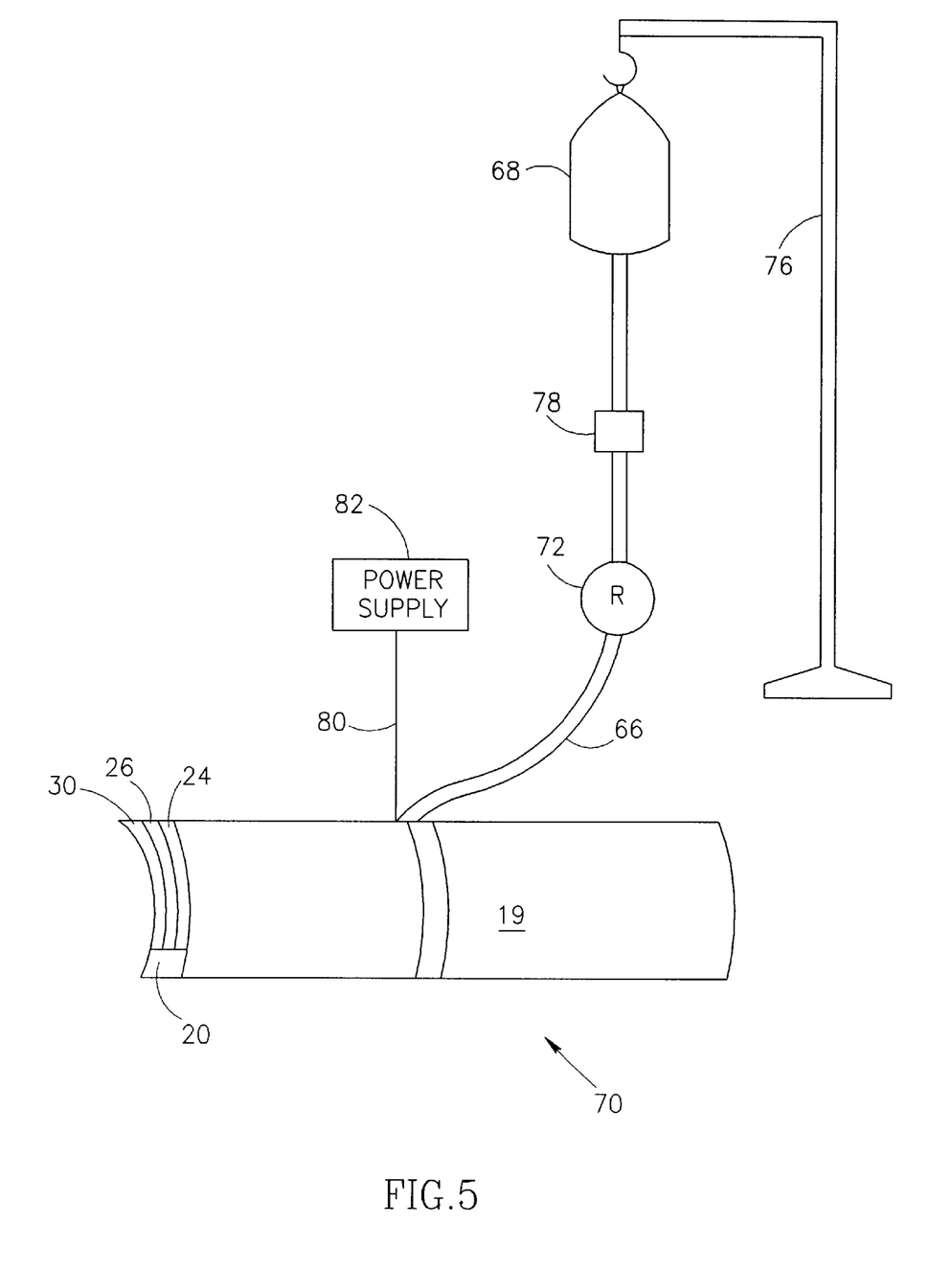
FIG. 5 is a diagram showing an assembly of a complete drug delivery system with the electrophoretic cuff of the invention.

FIG. 5 shows an overview of a preferred embodiment of cuff wrap apparatus 70 as used with a standard IV drip bag and pole stand. Stand 76 holds reservoir 68, allowing fluid to drip through drip chamber 78 to pump and titration regulator 72. Tubing 66 leads the fluid into cuff wrap apparatus 70 to patches 20. Harness wires 80 from power source 82, also leading into patches 20 provide electricity for electrophoresis, magnetophoresis, electrostimulation and pain sedation. Patches 20 are comprised of sealant 22, microtitration foam 24, porous electro-conductive membrane 26 and are equipped with biosensors 30.

Figure 6:
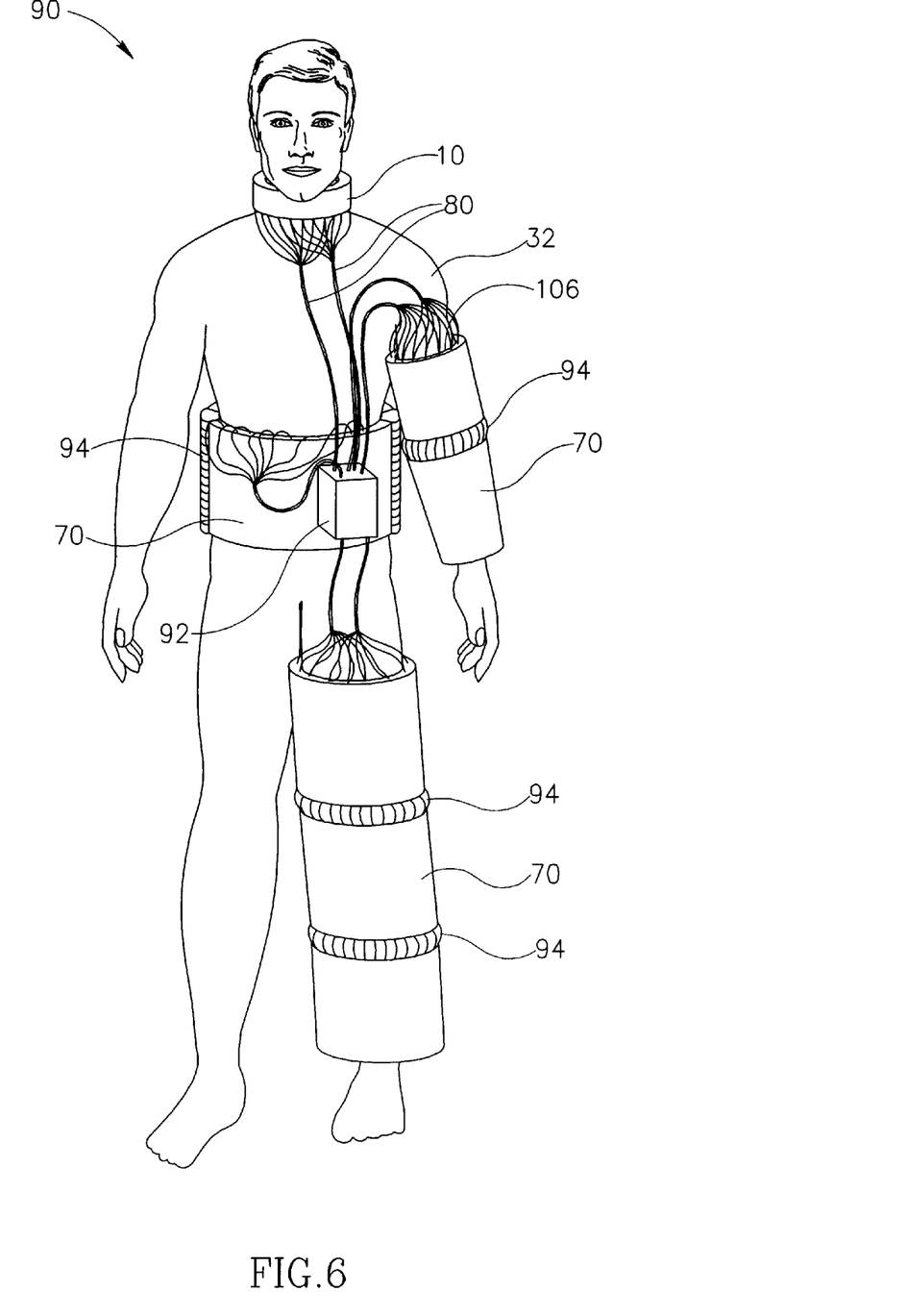
FIG. 6 is a front elevational view pictorially illustrating the electrophoretic cuff apparatus of the invention as applied to selected portions of the human body, including neck, arm, lower back and leg.

Referring now to FIG. 6, there is illustrated a pictorial representation of an electrophoretic cuff system 90 in accordance with this invention. The electrophoretic cuff system 90 is typically shown at selected anatomical locations on a human body.

System 90 is comprised of a flexible cuff 70 for wrapping around a body part or limb, a portable operating console 92 that incorporates a power supply source and a cable harness 80 for conductively coupling the console 92 to the cuff wrap 70.

Figure 7:
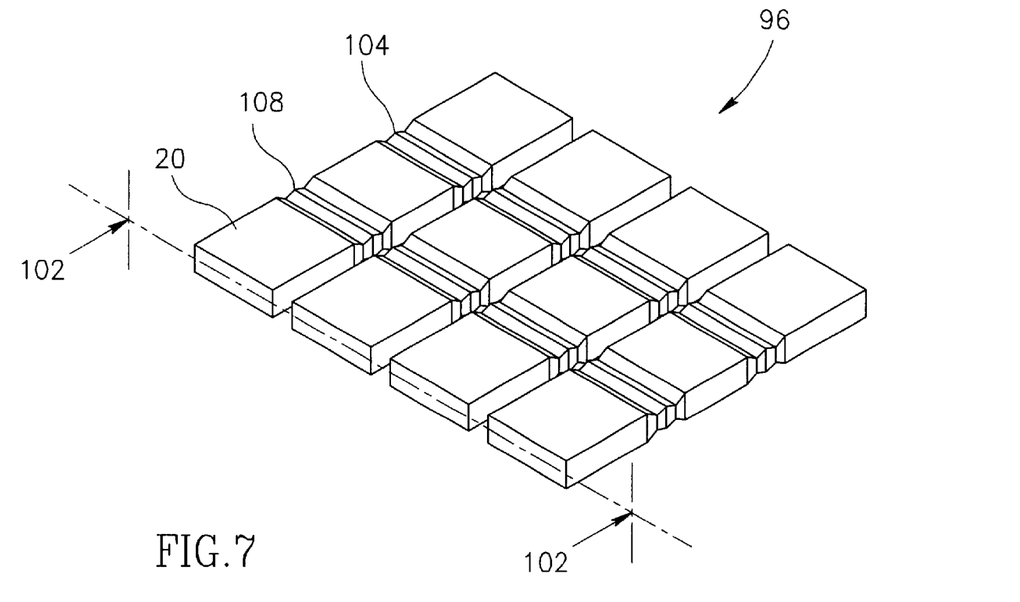
FIG. 7 is a perspective view of a portion of an applicator patch unit in conjunction with the apparatus of the invention illustrating a grid of transdermal patch devices.
Figure 8:
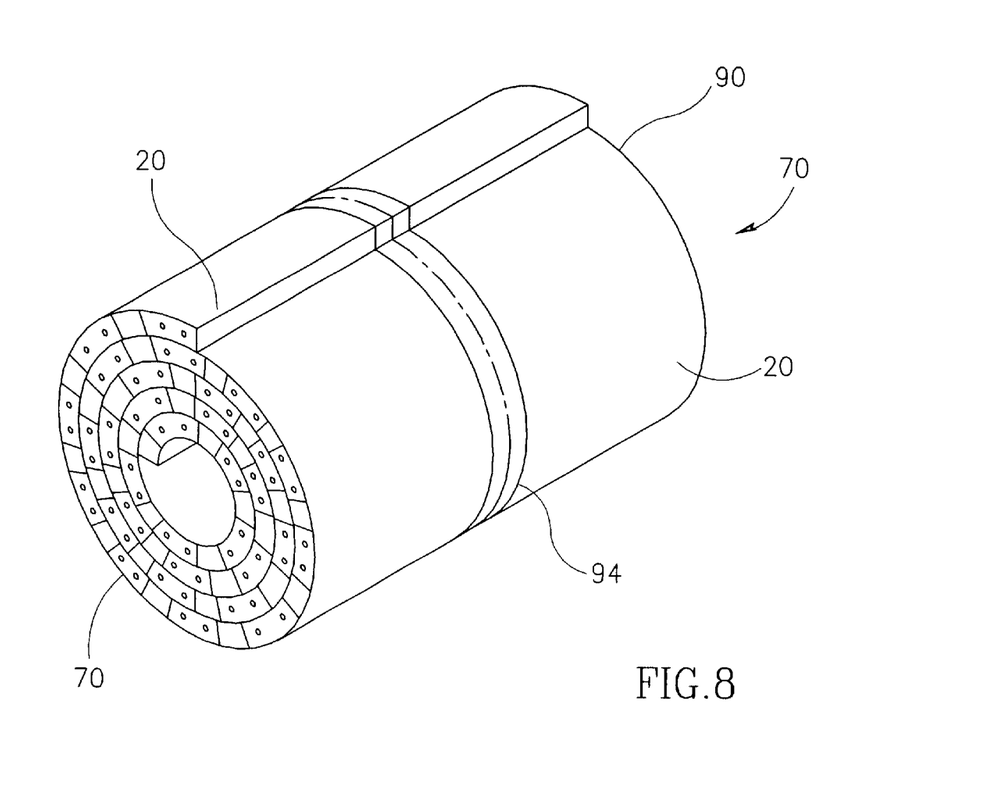
FIG. 8 is a perspective view of a portion of a patch connected to other patches forming a cuff in a stored configuration.
Figure 9A:
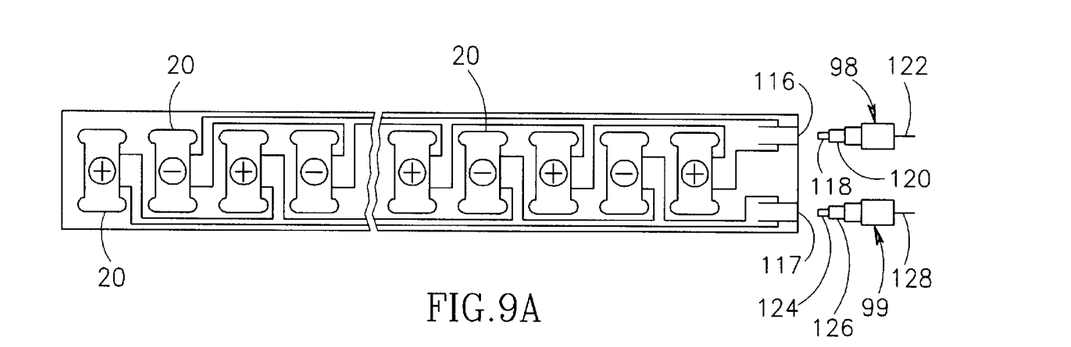
FIG. 9a is an elevational view, in enlarged scale, of a portion of the applicator cuff, showing the electrical circuitry for energizing the transdermal patch devices.

Flexible cuff wrap 70, as best shown in FIGS. 6, 7 and 8, is fabricated from a plastic and/or canvas garment-like fabric, having linked patch units 96 connected by Velcro strapping 94 as a closure for securing cuff wrap 70 against afflicted areas on the patient's body, for example, as shown in FIG. 6. Linked patch units 96 provide the required flexibility when applied around or on a body part, and are compliant when attached to another set of linked patch units 96 by Velcro strapping 94 and connected by electrical connector plugs 98, 99 (FIG. 9a) and fluid-flow connectors 100 (FIG. 9c).

In a preferred embodiment, the patch structure of unlinked patch devices 20 or autobiofuel powered transdermal patch devices 40 can be provided in a size conforming to individual patches of linked patches 96 to function in a cuff apparatus. The layered structure remains the same. In FIG. 7, a plurality of transdermal patch devices 20 are positioned within each patch unit 96 such that a longitudinal axis 102 of the transdermal patch devices 20 is perpendicular to a transverse axis 104 of cuff wrap 70. Transdermal patch devices 20 function as a porous electroconductive membrane layer. Contact surface 106 of cuff wrap 70 is intended for placement contiguous to the patient's skin 32. By way of example, transdermal patch devices 20, such as shown in FIG. 7, are rectangular, approximately ⅜ in. on each side and are spaced apart at point 108 approximately 2:1 ratio center to center, to provide about four transdermal patch devices 20 per square inch within the cuff wrap 70.

Figure 10:
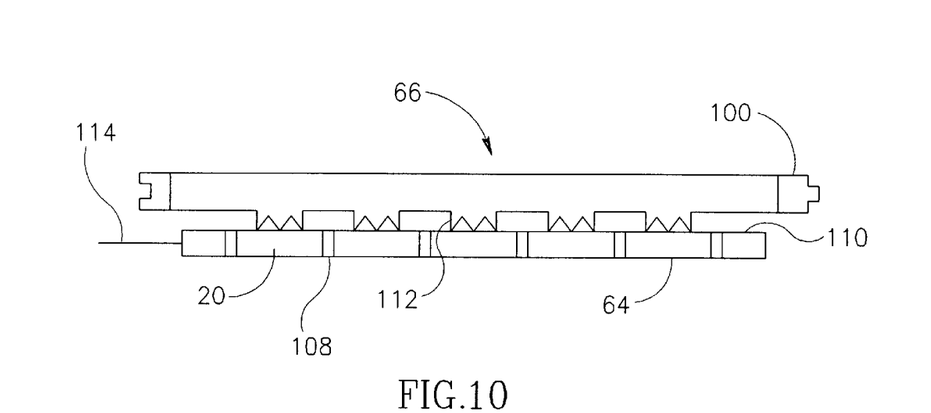
FIG. 10 shows a schematic drawing of a side view cross-section, showing the electrodes and supply tubes for delivering the fluid medium to the transdermal patch devices via a system of branching ducts.

Furthermore, transdermal patch devices 20 can be embedded in the plastic material during the manufacturing process, and are thus secured in place by the surrounding plastic material. Alternatively, as shown in FIG. 10, electrophoretic tubing 66 and tubing connectors 100 pass on top of, and are superior to, surface 110 of transdermal patch devices 20, simultaneously as they connect with the electrodes via duct system 112.

Further in connection with the fabrication of cuff wrap 70, it should be observed that before transdermal patch devices 20 are fixed into position, inside wiring 122,128 and electrophoretic tubing 66 are placed against the inside face of a waterproof substrate and/or canvas-like fabric forming the apparatus matrix, to prevent "leakage" of medicated or non-medicated fluid outside the aforementioned cuff.

Figure 9B:
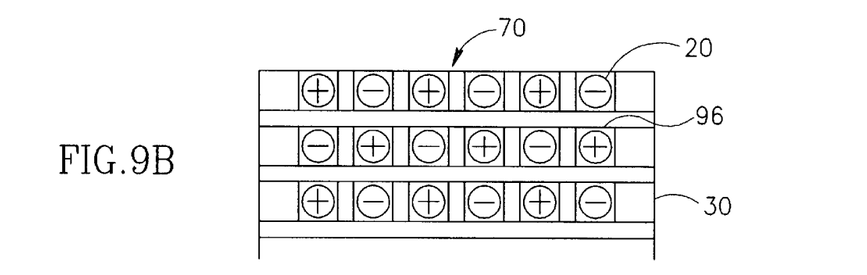
FIG. 9b is a top view of a portion of an applicator wrap used in conjunction with the apparatus of the invention, illustrating a "checkerboard" pattern of positive and negative electrically charged electrodes.
Figure 9C:
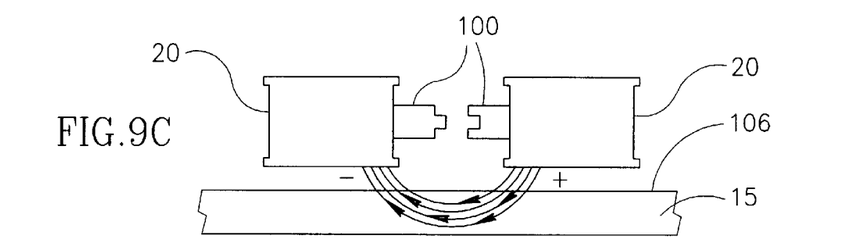
FIG. 9c is an elevational view showing the combined lines of positive and negative electron flow, or the electrical charge of opposite polarity associated with the apparatus.

Referring once again to transdermal patch devices 20, it will be noted that in FIG. 9 the wiring sequence for each transdermal patch device 20 provides for a current flow through adjacent electrodes to thereby generate a "checkerboard" of electrical currents of alternate polarities, as graphically depicted in FIG. 9b. This is accomplished by conductively coupling the wiring in two circuits, as will be further described herein. It will be appreciated by those skilled in the art that the inside wiring within transdermal patch device 20 can be comprised of an electroconductive polymer membrane. A wire harness 80, as shown in FIG. 6, is conductively coupled to transdermal patch devices 20 by a set of (two-conductor) connector plugs 98, 99 that are accommodatingly received within a corresponding set of sockets 116, 117.

Referring to FIG. 9a, it will be seen that the set of connector plugs 98, 99 are comprised of portions 118, 120, 122 and 124, 126, 128, respectively. The portions 118, 120 and 124, 126, when inserted within the respective sockets 116, 117 complete circuits for energizing the electrodes. As seen in FIG. 9c, it will be noted that when the current flows in a clockwise direction in the transdermal patch devices 20 in one circuit defined by connector plug 98, the current will correspondingly flow in a counterclockwise direction through the electrodes within the other circuit defined by connector plug 99.

Figure 11:
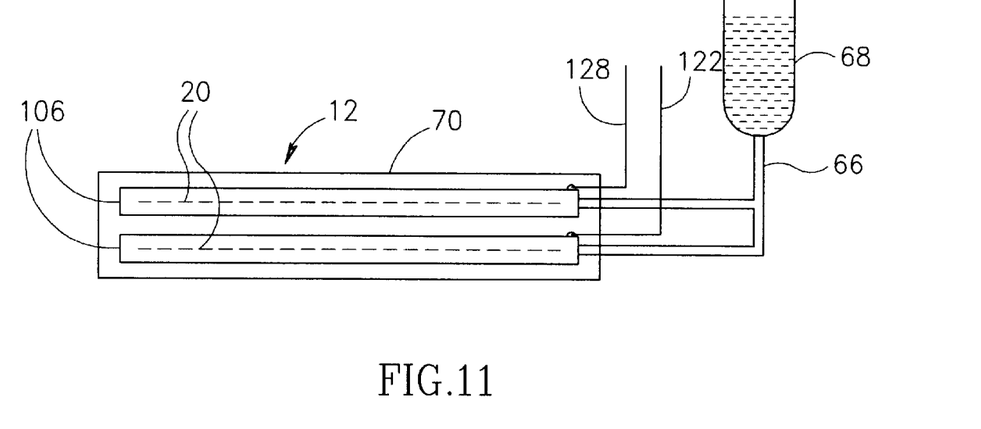
FIG. 11 is a cross-sectional view of an electrophoretic pharmaceutical delivery system with a fluid reservoir connected to the apparatus.

In FIG. 11 there is shown an electrophoretic pharmaceutical delivery system with fluid reservoir 68. Electrophoretic cuff 70 can induce a pharmaceutical fluid flow when simultaneously placed under a cast or brace with additional treatment modalities of electrostimulation. In addition, pain sedation can be provided by nerve stimulation analgesia, and galvanic muscle strengthening can be provided by producing muscle contraction that deters the onset of atrophy in a body part. The electrostimulation regimen is also effective for reversing the degenerative effects of atrophy.

This aspect of the invention uses transdermal patch devices 20 as conductive stimulator pads. Transdermal patch devices 20 are applied to contact surface 106 of cuff wrap 70. Connector plugs 98, 99 provide transdermal patch devices 20 with opposite charges of DC current. When cuff wrap 70 is placed on the patient, transdermal patch devices 20 are in direct contact with the skin surface.

The previously described muscular electrostimulation and interferential microcurrent therapy can be used independently or in combination with the electrophoretic therapy delivery system.

The purpose of the iontophoresis is to utilize an electrical field to influence the transfer and metabolism of the drug medium into the patient's body, as shown in FIG. 1. For this purpose, transdermal patch devices 20 include a porous material that is connected by a network of tubing 66 supplied with a selected drug medium from reservoir 68 through a gravity feed system. It should be further noted that transdermal patch devices 20 will at all times be oppositely charged. In operation, transdermal patch devices 20 provide the function of receiving the pharmaceutical medium from branch tubing 66. The fluid medium is distributed throughout transdermal patch devices 20 by capillary action.

Figure 12:
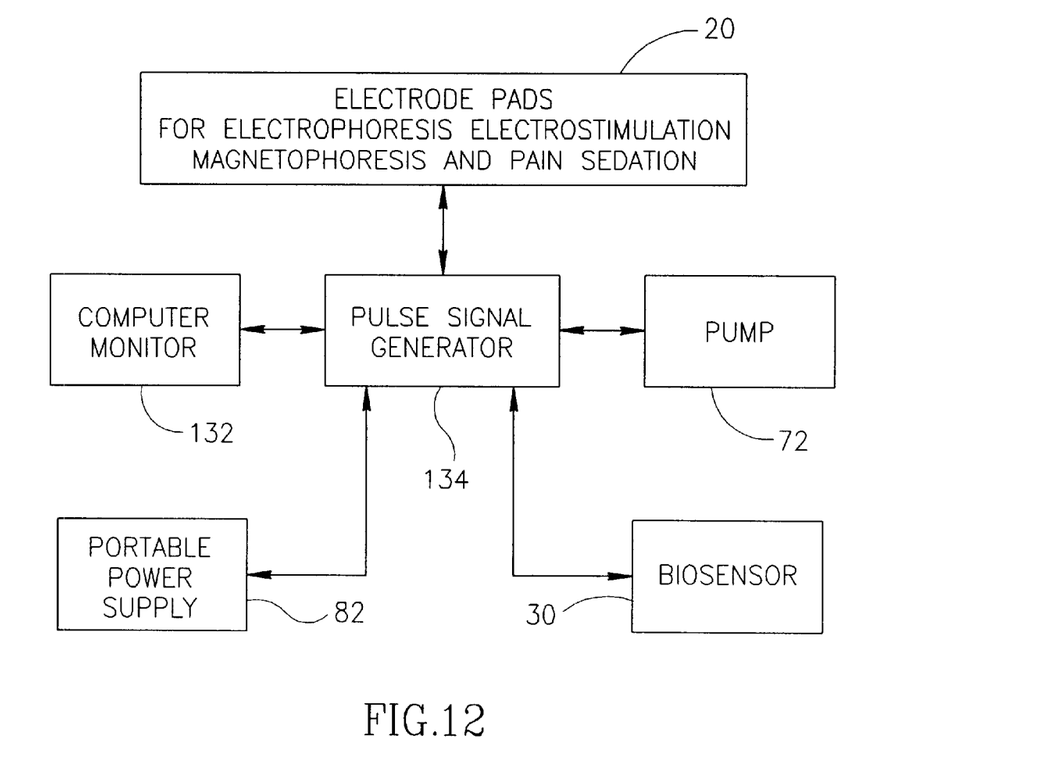
FIG. 12 is a block diagram of the invention showing the transdermal patch system within the system components.

As shown in FIG. 12, the application of the electrical current from power supply 82 provides an ionization effect producing a more effective delivery path to the patient. This is particularly advantageous when a conventional cast or brace has been placed over cuff wrap 70 and thus the afflicted area is otherwise inaccessible to direct drug therapy.

With regard to the electrophoretic pharmaceutical delivery system, a computerized chip and monitor 132 in a fluid distribution system monitors and supplies the medicated fluid from external bag reservoir 68 at various desired titration rates of ml/second through regulating pump 72. Rate of flow needed is determined by biosensor 30, and regulates fluid flow to increase efficiency to perform iontophoresis. Pulse signal generator 134 receives power from power supply 82 to provide pulses to transdermal patch devices 20 for electrostimulation, magnetophoresis, electrophoresis and pain sedation.

Figure 13:
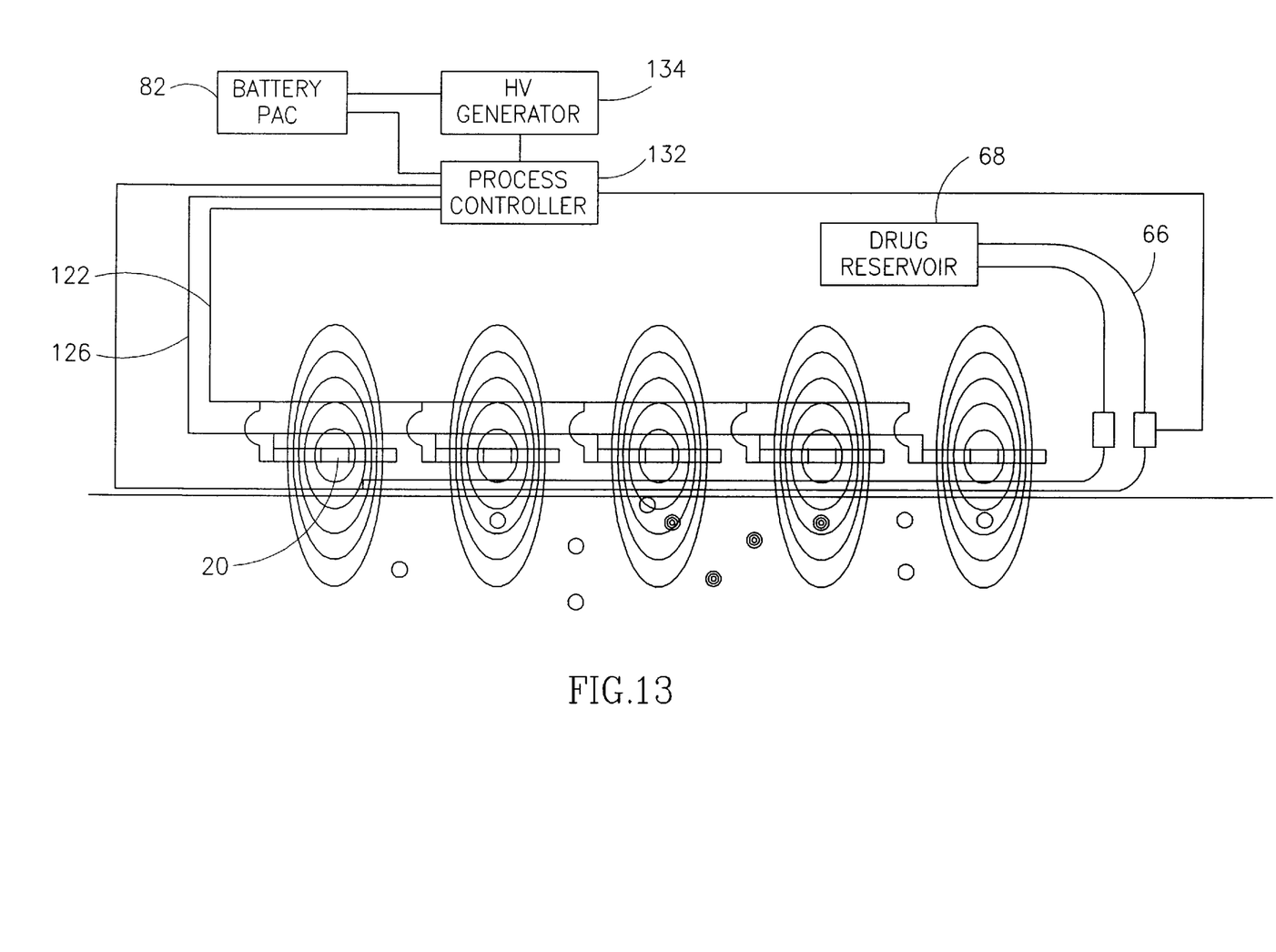
FIG. 13 shows a schematic drawing of a side view cross-section showing the electromagnetic electrodes to create the drive mechanism for magnetophoresis.

Referring now to FIG. 13, there is shown a schematic drawing in which transdermal patch devices 20 are supplied as electromagnetic electrodes and are arranged to create the drive mechanism for magnetophoresis. Magnetic fields generate an electrical field within the tissue which is perpendicular to the magnetic field. This magnifies the electrical field strength, thereby increasing the penetration factor without increasing the externally applied current. This method produces a homogeneous potential layer.

When the electrocurrent drivers are combined with electromagnetic fields with an electrophoretic current, the driving force to increase drug delivery through membranes is greatly enhanced. The effects of pulsed electromagnetic fields (PEMF) or "the electromagnetic phenomenon" are explained by the changes in the distribution of electrostatic charges near the membrane protein-protein binding sites. In the present invention, the process of combining PEMF and electric currents for transdermal drug delivery through a membrane electrode carrier has been termed "electroinfusion" (c). The electro-infusion technique creates greater absorption and depth penetration of a permeant to a target area. In addition the use of PEMF's assists in localization of the drug to a specific target area. When a multiple array of membrane electrodes are arranged on an anatomical area in a cylindrical fashion perpendicular to the SC forming cuff wrap 70, a high rate of drug delivery to a specific treatment area will result.

By having a multiple arrangement of transdermal patch devices 20 delivering the permeant over a large circumference, an alternating sequence is consecutively changing the infiltration area. The end result of this is avoidance of skin irritation. The living tissue is protected while ionic shift is eliminated, allowing increased penetration of ions. It is possible to transfer simultaneously several types of permeants which have inverse polarities.

Preferred power supply 82 is an electrochemical cell such as a commercially available nickel cadmium or lithium 9 volt rechargeable battery. The battery is housed within console 92 (see FIG. 6). Pulse generator 134 is included within console 92. Generator 134 supplies DC electrical power for electrostimulation and for the electrophoretic pharmaceutical delivery system.

It should be noted that pulse generator 134 can be modulated to provide a scale of electrical and electromagnetic field intensities, alternating polarities, timing and strengths that can be automatically, consecutively, and/or specifically programmed in accordance with the desired electrostimulation therapy.

The signals utilized in connection with the electrophoretic system include DC current modulation having trapezoidal, square and sinusoidal wave pulses from 0–50 volts with alternating and continuous pulses modulated at between 1 to 200 Hertz and the electrical current ranging from 0–500 mA, with a current range from 0–15 mA responsible to perform iontophoresis. For iontophoresis, the mode can vary 50% on, 50% off or as desired. For neuromuscular stimulation, the pulses have a 20–30% off and 70–80% on timing for maximum effectiveness.

The present embodiment is therefore to be considered in all respects as illustrative and not in a restrictive sense, the scope of the invention being indicated by the appended claims rather than by the foregoing description and all changes which come within the meaning and range of equivalency of the claims are therefore intended to be embraced therein.

We claim:

1. A transdermal patch device for delivery of a pharmaceutical medium comprising:

a stored energy source for generating an electrical current;

means for generating an electromagnetic field having at least one predetermined frequency, means for activating said energy source to generate said current producing said electromagnetic field;

a layer of permeable foam for retaining therein a quantity of pharmaceutical medium exhibiting at least partial ionization; and an electroconductive membrane disposed under said foam layer through which the pharmaceutical medium passes, said electromagnetic field driving said ionized pharmaceutical medium by active transport through said membrane to provide drug treatment therapy via the skin.

2. The device of claim 1 further comprising an electrophoretic tubing port in fluid communication with said layer of permeable foam defining a refillable storage reservoir, said port introducing the pharmaceutical medium into said patch device.

3. The device of claim 2 wherein said port is shaped to accommodate a drug-filled syringe for injecting pharmaceutical medium into said foam.

4. The device of claim 1 further comprising a biosensor integrated within said electroconductive membrane for sensing a quantity of the pharmaceutical medium passing therethrough and developing a responsive signal.

5. The device of claim 4 wherein said biosensor comprises:

a set of spaced apart electrode plates, comprising a reference electrode, an analyzing electrode, and a comparison electrode, said analyzing electrode disposed proximate a treatment area, said reference electrode disposed away from said treatment area, and said comparison electrode disposed between said analyzing and reference electrodes closer to said reference electrode, said responsive signal being a voltage representing the difference in voltage differentials measured between said reference electrode and each of said analyzing and comparison electrodes.

6. The device of claim 4 wherein said biosensor additionally monitors levels of chemicals in the blood so as to determine and justify delivery of drug dosages.

7. The device of claim 1 wherein said electroconductive membrane further comprises a dense coating layer disposed on said membrane having at least one of fixed negative and positive charges in a mosaic pattern for controlling said drug delivery through said membrane.

8. The device of claim 1 wherein said dense coating layer is at least partially comprised of at least one of sulfonated polysulfone and polyetheretherketone.

9. The device of claim 1 wherein said patch can adhere to a skin surface for local area drug delivery.

10. The device of claim 1 wherein said stored energy source is provided as a fuel cell.

11. The device of claim 10 wherein said means for activating comprises a depressable activator button which activates said fuel cell.

12. The device of claim 1 wherein said stored energy source is provided as a battery.

13. The device of claim 12 wherein said means for activating comprises a depressable activator button which completes an electrical circuit for generating said current.

14. The device of claim 1 wherein said means for generating an electromagnetic field is provided as an impermeable conductive plate providing a barrier for preventing leaching of components of said energy source through said membrane to a treatment area.

15. The device of claim 1 in which said electric current generates magnetic and electric fields providing a drive mechanism for transdermal magnetophoresis and iontophoresis of the pharmaceutical medium.

16. The device of claim 1 in which said electric current is combined with said electromagnetic field to develop transdermal electro-infusion of the pharmaceutical medium.

17. The device of claim 1 in which said electric current provides electrostimulation therapy.

18. The device of claim 1 in which said pharmaceutical medium is a chemotherapy drug for electrochemotherapy.

19. The device of claim 1 wherein a multiple quantity of said transdermal patch devices are linked together as a cuff for cumulative drug treatment of a limb.

20. The device of claim 19 configured within an electrophoretic cuff apparatus, said apparatus comprising:

an applicator wrap of single or multiple connecting patch units each containing a plurality of said transdermal patch devices;

means for simultaneously generating an electric current in each of said patch devices, and a network of electrophoretic tubing adjacent to a surface of said patch devices for delivering a selected pharmaceutical medium to said patch devices, said patch devices being selectively energized by said electric current for providing drug treatment therapy.

21. The device of claim 20 wherein said patch units are connected to a slow drip liquid drug reservoir through a pump connected to said electrophoretic tubing with a system of duct distribution to each and every individual porous patch unit to deliver a drug through the skin and surface tissues.

22. The device of claim 21 further comprising a computerized control system for regulating flow from said slow drip liquid reservoir through said pump to said electrophoretic tubing, in accordance with said responsive signal.

23. The device of claim 1 further comprising regulation means for controlling passage of said pharmaceutical medium through said membrane in accordance with said responsive signal, to regulate and permeate said pharmaceutical medium in a treatment area by active transport transdermally.

24. The device of claim 23 wherein said regulation means comprises a computerized control system.

25. The device of claim 23, wherein said computerized control system comprises a display readout of a flow rate of said pharmaceutical medium.

26. A method of providing transdermal therapy of a pharmaceutical medium comprising the steps of:

providing a transdermal patch device comprising:

a stored energy source for generating an electrical current, means for generating an electromagnetic field having at least one predetermined frequency;

means for activating said energy source to generate said current producing said electromagnetic field;

a layer of permeable foam for retaining therein a quantity of pharmaceutical medium exhibiting at least partial ionization; and an electroconductive membrane disposed under said foam layer through which the pharmaceutical medium passes, and activating said energy source for generating said current to produce said electromagnetic field, said electromagnetic field driving said ionized pharmaceutical medium through said membrane by active transport to provide drug treatment therapy via the skin.

27. The method of claim 26 wherein said step of activating said energy source generates electrical and electromagnetic field intensities having alternating polarities and predetermined sequential intervals programmed to correspond to selected drug characteristics.

28. The method of claim 27 wherein said various modulated electrical and electromagnetic fields are generated on a scale of intensities.

29. The method of claim 26 wherein the pharmaceutical medium is provided within said layer of permeable foam by a method comprising the steps of:
   providing an electrophoretic tubing port in fluid communication with said layer of foam; and
   inserting the pharmaceutical medium into said layer of foam via said port.

30. The method of claim 29 wherein said step of inserting is performed using a pharmaceutical medium administered in at least one of combinational and sequential forms.

31. The method of claim 26 further comprising the steps of:
   providing an electrophoretic cuff apparatus comprising:
      an applicator wrap of single or multiple connecting patch units containing a plurality of said transdermal patch devices;
      means for simultaneously generating an electric current in each of said patch devices, and
      a network of electrophoretic tubing adjacent to a surface of said patch devices;
   delivering a selected pharmaceutical medium to said patch devices, said patch devices being connected to a controlled slow drip liquid reservoir through said network of tubing with a system of duct distribution to each and every individual patch device; and
   selectively energizing said patch devices by said electric current to provide said drug treatment therapy through the skin and surface tissues.

32. The method of claim 31 wherein said delivering step is performed by a computerized control system in accordance with said responsive signal.

33. The method of claim 32 wherein said step of selectively energizing said patch devices establishes at least one of anode and cathode drug delivery modes.

34. The method of claim 31 wherein said step of selectively energizing said patch devices provides a DC current modulated in at least one of trapezoidal, square and sinusoidal wave pulses from 0–50 volts with alternating and continuous wave pulses modulated between 50 and 200 Hz and the electrical current ranging from 0 to 50 mA, within a current range of 0 to 15 mA.

35. The method of claim 31 wherein said step of selectively energizing said patch devices provides a DC electromagnetic current modulated in a format of at least one of trapezoidal, square and sinusoidal wave pulses from 0–50 volts with alternating and continuous pulses modulated between 0 to 200 Hz and the electrical current ranging from 0 to 50 mA, within a gauss range from 0–100 Gauss.

36. The method of claim 34, wherein said pulses are generated as at least one of two types, combined and individual.

37. The method of claim 35, wherein said pulses are generated as at least one of two types, combined and individual.

38. The method of claim 31 further comprising the step of providing a computerized control system for regulating flow from said slow drip liquid reservoir through said tubing.

* * * * *